United States Patent [19]

Agostini

[11] Patent Number: 6,080,793
[45] Date of Patent: *Jun. 27, 2000

[54] COSMETICALLY/PHARMACEUTICALLY/ HYGIENICALLY-ACTIVE SUPPLE DOUGHS COMPRISING HEAT-SENSITIVE COMPOUNDS

[75] Inventor: Isabelle Agostini, Chatenay Malabry, France

[73] Assignee: Societe L'Oreal S.A., Paris, France

[*] Notice: This patent is subject to a terminal disclaimer.

[21] Appl. No.: 09/328,788

[22] Filed: Jun. 9, 1999

Related U.S. Application Data

[62] Division of application No. 08/687,996, Jul. 29, 1996, Pat. No. 5,936,002.

[30] Foreign Application Priority Data

Jul. 28, 1995 [FR] France .................................. 95 09255

[51] Int. Cl.$^7$ ............................. A61K 47/30; B29C 47/38
[52] U.S. Cl. .................... 514/772.1; 424/401; 514/772.3; 514/772.6; 514/789; 514/950; 514/970; 264/519; 264/540; 264/176.1; 264/211; 264/211.21; 264/DIG. 65

[58] Field of Search ........................ 424/401; 514/772.1, 514/772.3, 772.6, 789, 950, 970; 264/519, 540, 176.1, 211, 211.21, DIG. 65

[56] References Cited

U.S. PATENT DOCUMENTS

| 4,164,563 | 8/1979 | Chang ........................................ 424/83 |
| 5,045,325 | 9/1991 | Lesko et al. ................................. 426/5 |
| 5,897,869 | 4/1999 | Roulier et al. ........................... 424/401 |

FOREIGN PATENT DOCUMENTS

| 0530084 | 3/1993 | European Pat. Off. . |
| 0530085 | 3/1993 | European Pat. Off. . |

*Primary Examiner*—Frederick Krass
*Attorney, Agent, or Firm*—Burns, Doane, Swecker & Mathis, L.L.P.

[57] ABSTRACT

Cosmetic/pharmaceutical/hygienic compositions (e.g., lipcolors) are formulated as homogeneous and stable, supple dough extrudates, said supple dough extrudates having at least one thermally-unmodified but normally heat-sensitive compound (for example a volatile compound and/or a compound having a low flash point) and at least one elevated melting temperature T compound (for example a wax) homogeneously distributed therethrough.

7 Claims, No Drawings

COSMETICALLY/PHARMACEUTICALLY/ HYGIENICALLY-ACTIVE SUPPLE DOUGHS COMPRISING HEAT-SENSITIVE COMPOUNDS

CROSS-REFERENCE TO COMPANION APPLICATIONS

This application is a divisional of application Ser. No. 08/687,996, filed Jul. 29, 1996, now U.S. Pat. No. 5,936, 002.

Copending applications Ser. No. 08/688,027 and Ser. No. 08/690,643 each filed concurrently herewith and each assigned to the assignee hereof.

BACKGROUND OF THE INVENTION

1. Technical Field of the Invention

The present invention relates to novel compositions, notably for topical cosmetic applications, formulated as supple doughs which are useful for the care and/or makeup of the lips and/or of the skin.

This invention also relates to a process for the preparation of such compositions.

2. Description of the Prior Art

Compositions, especially cosmetic formulations, that can be topically applied to the skin or the lips as a makeup or care product, such as, for example, the bases for lips or lipsticks, generally contain fatty substances, including waxes, pigments and/or fillers and, optionally, adjuvants and additives. Cosmetic compositions are also known to this art which are in the form of supple doughs that can be applied with the aid of a brush, for example. These compositions generally contain no or little wax, especially in a minor amount, and this allows them to be picked up and applied with ease.

Compositions too are known in which at least a proportion of the oils is replaced with volatile oils. This permits improving, inter alia, the behavior of the film, by concentration of the constituents on evaporation of the volatile compounds after application.

According to the prior art, such compositions are generally formulated by hot mixing, generally at a temperature on the order of 95°–100° C., of the various constituents with the exception of the volatile oils, and then introducing said volatile oils at a mixing temperature which is less high but nevertheless on the order of 75°–80° C. Indeed, it is not possible to incorporate the volatile oils into a "cold" mixture without the crystallization and setting solid of said waxes.

Such prior art process entails, on the one hand, a loss due to evaporation of a proportion of the said volatile oils during the formulation of the composition, so that the amount to be added is required to be increased beforehand in order to attain the desired final concentration. On the other hand, the handling at an elevated temperature of potentially explosive volatile oils of low flash point is a rather dangerous procedure.

SUMMARY OF THE INVENTION

Accordingly, a major object of the present invention is the provision of an improved technique which avoids or conspicuously ameliorates the above disadvantages and drawbacks to date characterizing the state of this art, whereby volatile and low flash point compounds are formulated into compositions including constituents of high melting temperature, especially under "cold" conditions, to prepare a wide variety of cosmetically/therapeutically useful homogeneous supple doughs therefrom.

Briefly, the present invention features the preparation of cosmetic, pharmaceutical or hygienic compositions including at least one heat-sensitive compound, comprising formulating said at least one heat-sensitive compound into the composition by means of an extruder.

This invention also features compositions prepared via the above process, in the form of supple doughs which comprise at least one heat-sensitive compound and a wax.

DETAILED DESCRIPTION OF BEST MODE AND SPECIFIC/PREFERRED EMBODIMENTS OF THE INVENTION

More particularly according to the present invention, the subject homogeneous compositions, which are useful in the fields of cosmetics, pharmaceuticals and hygiene, comprise, on the one hand, compounds which have a melting temperature T and, on the other, compounds which it is not possible to heat to this temperature T, deemed compounds which are "sensitive" to the temperature T, for example because they become denatured or volatilize thereat.

Thus, this invention is especially applicable for the production of makeup products and notably for the preparation of products which contain waxes and volatile compounds, such as colored lip makeup.

By the "sensitive" temperature of the compound is intended the temperature at which, for example, it volatilizes or becomes denatured, or is otherwise thermally modified, i.e., the temperature beyond which it is not possible to heat without initiating deterioration thereof, or effecting a change in state or alteration in its composition, its chemical nature, its structure, and the like.

This invention thus features the formulation of compositions which comprise waxes, compounds of "elevated" melting temperature and heat-sensitive compounds, especially compounds which are volatile and/or of low flash point.

By "volatile compound" is intended any compound capable of evaporating on contact with the skin.

By "volatile compound of low flash point" is intended any compound whose flash point is lower than approximately 100° C. and especially of flash point ranging from 30° to 85° C., namely, capable of being ignited in the presence of a spark at a usual temperature employed during the preparation of compositions including waxes.

Exemplary volatile compounds of low flash point include certain hydrocarbon or linear or cyclic silicone oils such as cyclotetradimethylsiloxane (flash point 55° C.), cyclopentadimethylsiloxane (flash point approximately 77° C.), cyclohexadimethylsiloxane (flash point 76° C.), methylhexyldimethylsiloxane (flash point 79° C.) and isoparaffins (flash point 56° C.). These oils may be employed either alone or in admixture.

The waxes which may be present in the subject compositions preferably have a melting point higher than 55° C. and a needle penetration number at 25° C. which preferably ranges from 3 to 40. Exemplary such waxes, employed either alone or in admixture, include animal, vegetable, mineral and synthetic waxes such as beeswax, carnauba, candelilla, ouricury and Japan wax, cork fiber or sugarcane waxes, paraffin and lignite waxes, microcrystalline waxes, ozokerites, polyethylene waxes and the waxes obtained via Fischer-Tropsch synthesis, and silicone waxes.

It has been determined that, although the compositions according to the invention may include a large amount of waxes, preferably on the order of 12%–60% by weight, it is possible to incorporate volatile compounds into same when cold, in the absence of any onset of crystallization of said waxes. It is thus possible to formulate a homogeneous and stable supple dough.

The compositions of the invention may also comprise volatile oils of high flash point, especially whose flash point is higher than 100° C., and/or nonvolatile, silicone and/or hydrocarbon oils, whether alone or in admixture, as well as any other fatty substance which is conventional in the cosmetic field.

Exemplary such silicone oils include the polydimethylsiloxanes, phenylated silicone oils, especially polyphenylmethylsiloxanes, and the phenyltrimethicones, or mixtures thereof, and in particular the phenylated silicone oils having the following structural formula (I):

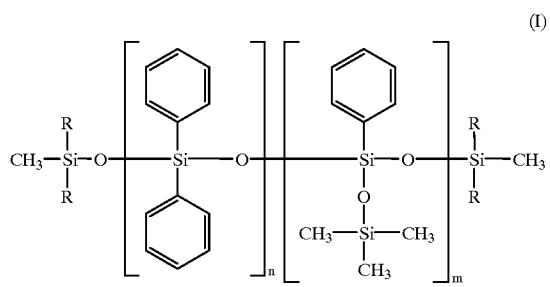

in which R is a $C_1$–$C_{30}$ alkyl radical, an aryl radical or an aralkyl radical; n is an integer ranging from 0 to 100; and m is an integer ranging from 0 to 100, with the proviso that the sum m+n ranges from 1 to 100.

R is preferably a methyl, ethyl, propyl, isopropyl, decyl, dodecyl or octadecyl radical, or else a phenyl, tolyl, benzyl or phenethyl radical.

Exemplary of these phenylated oils are the Belsil PDM1000 oil marketed by Wacker, the DC556 and SF558 oils marketed by Dow Corning, the Abil AV8853 oil marketed by Goldschmidt or the Silbione 70633V30 oil marketed by Rhône Poulenc.

Also exemplary are vegetable, mineral, animal and/or synthetic oils such as liquid paraffin, liquid petrolatum, perhydrosqualene, arara, sweet almond, calophyllum, palm, castor, avocado, jojoba, olive or wheat germ oil, fatty acid esters, alcohols, acetylglycerides, alcohol or polyalcohol octanoates, decanoates or ricinoleates and fatty acid triglycerides.

The subject compositions may also contain, in particular, pigments and/or "mothers-of-pearl" and/or fillers which are typically employed in cosmetic compositions. The pigments may be white or colored, inorganic and/or organic. Exemplary inorganic pigments include titanium, zirconium or cerium dioxides and zinc, iron or chromium oxides and ferric blue. And exemplary organic pigments include carbon black and barium, strontium, calcium and aluminum lacquers.

The mothers-of-pearl may be selected from among mica coated with titanium oxide, with iron oxide, with natural pigment or with bismuth oxychloride, as well as colored titanum mica.

The fillers may be inorganic or synthetic, lamellar or nonlamellar. Exemplary thereof are talc, mica, silica, kaolin, nylon and polyethylene powders, Teflon, starch, micatitanium, natural mother-of-pearl, boron nitride, microspheres such as Expancel (Nobel Industrie), polytrap (Dow Corning) and silicone resin microbeads (for example Tospearls marketed by Toshiba).

The subject compositions may additionally comprise any additive or adjuvant typically employed in the cosmetic field, such as antioxidants, perfumes, essential oils, preservatives, cosmetic active substances, hydrating or moisturizing agents, vitamins, essential fatty acids, sphingoceryls, sunscreens, surfactants, liposoluble polymers such as hydrocarbon polymers and especially polybutene, polyalkylenes, polyacrylates and silicone polymers which are compatible with the fatty substances.

The relative proportions of each of the constituents of the compositions according to the invention may be determined by one skilled in this art on the basis of his or her general knowledge and on the basis of the prior art, according to the intended application of the composition, taking care that the selection of these constituents and/or their quantity does not, or substantially does not, deleteriously affect the advantageous properties of the subject compositions.

The compositions of this invention may be in the form of a supple dough whose viscosity can be measured, in contrast to the solid structure of a rod or stick, whose viscosity cannot be measured. Their dynamic viscosity at 25° C. generally ranges from 3 to 35 Pa·s, measured using a Contraves TV rotary viscometer fitted with an "MS-r4" rotor, at a frequency of 60 Hz.

The compositions according to the invention may thus be in the form of a product for making up the skin and/or the lips. In particular, they may be in the form of a foundation, a blusher or an eyeshadow, or of a colored lip makeup. When they contain drug species or biologically active agents, they may be in the form of a base for lip care. They may also be employed as a fixing base or fixative to be applied over a conventional colored lip makeup. The base then forms a protective film over the colored makeup film, limiting its transfer and migration, and thus permits its durability to be increased.

The compositions of this invention may also be in the form of a skincare product, a hygienic or pharmaceutical product, or else a sunscreen or artificial suntanning preparation.

To prepare the compositions of the invention, a premix is first formulated including at least a proportion of the various constituents thereof, including the compounds which have a melting temperature T which may be elevated, such as waxes, next heating this premix to a temperature at which it melts, all or a part of the other constituents being then added, as appropriate, either in a single dose or in several portions, and then, at a temperature which is lower than its/their "sensitive" temperature, the compound(s) which is (are) sensitive to the temperature T, as well as, optionally, the remainder of the constituents, is (are) added, while at the same time maintaining a blending of the mixture by means of an extruder.

Lastly, the mixture obtained is blended in the extruder over at least a proportion of its cooling time to the required temperature, generally the ambient temperature.

When the heat-sensitive compound is a volatile oil sought to be formulated into a composition including waxes, it is preferably introduced into the mixture at a temperature lower than 45° C., or even at ambient temperature.

The mixing operation is preferably also carried out in an extruder.

The heating, mixing, blending and cooling operations may be carried out entirely in an extruder or in several extruders, which will then be arranged in series.

However, a single twin-screw extruder is preferably employed to conduct the entirety of the process.

It too has been determined that the compositions obtained after extrusion exhibit a special softness and provide a certain sliding sensation when applied to the skin, while avoiding the appearance and the sensation of oily grease.

The conditions under which the extrusion may be carried out are described in FR-94/00756, hereby expressly incorporated by reference.

In order to further illustrate the present invention and the advantages thereof, the following specific example is given, it being understood that same is intended only as illustrative and in nowise limitative.

EXAMPLE

A colored lip makeup was formulated as a supple dough and had the following composition:

| (a) | cyclopentadimethylsiloxane | 40 g |
|---|---|---|
| (b) | polyphenylmethylsiloxane (DC556 Fluid from Dow Corning) | 20 g |
| (c) | waxes (silicone and polyethylene) | 25 g |
| (d) | pigments and fillers | 15 g |

These various ingredients, with the exception of the volatile oil, were introduced into a twin-screw extruder at an inlet temperature of approximately 75°–95° C.

The volatile oil was introduced into the extruder at the end of extrusion, at a temperature on the order of 20°–25° C.

At the outlet, a supple dough having a viscosity of 27 Pa·s was obtained, which was in the form of a stable and homogeneous single phase that could be picked up with the aid of a brush for topical application thereof.

This composition could be converted into a homogeneous film which was applied easily and which spread easily and uniformly. The film obtained had a light texture and remained comfortable to wear all day long Were it desired to formulate this same composition by a conventional process, it would be necessary to heat the various ingredients, except the volatile oil, to 95°–100° C. to melt the waxes, and next to preheat the volatile oil to approximately 65° C. and then to introduce it into the mixture at 75°–80° C. in order to prevent the waxes from resolidifying.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the formulation of a cosmetic/therapeutic composition comprising cosmetically or therapeutically acceptable constituents and at least one first compound having a determined melting temperature T and at least one second compound which is denatured or which volatilizes at said determined melting temperature T said process comprising the steps of:

preparing a premix including at least a fraction of said constituents and, said at least one first compound having said determined melting temperature T, heating said premix to said melting temperature T, blending said premix and then cooling the mixture obtained to a temperature lower than said melting temperature T and, at the same time, adding said at least one second compound thereto, said blending being carried out during said cooling until room temperature is reached and at least in part in at least one extruder.

2. The process as defined by claim 1, comprising heating and cooling in one extruder, or a plurality of extruders arranged in series.

3. The process as defined by claim 2, comprising heating, blending, and cooling in a single twin-screw extruder.

4. The process as defined in claim 1, wherein said first compound is selected from waxes having said determined melting temperature.

5. The process as defined in claim 1, wherein said second compound is selected from compounds which are volatile or compounds which have a flash point lower than 100° C.

6. The process as defined in claim 1, wherein said second compound comprises a cyclotetradimethylsiloxane, a cyclopentadimethylsiloxane, a cyclohexadimethylsiloxane, a methylhexyldimethylsiloxane, an isoparaffin, or mixture thereof.

7. The process as defined in claim 4, wherein said at least one wax comprises beeswax, carnauba, candelilla, ouricury or Japan wax, cork fiber or a sugarcane wax, a paraffin or lignite wax, a microcrystalline wax, an ozokerite, a polyethylene wax, a wax obtained via Fischer-Tropsch synthesis, a silicone wax, or combination thereof.

* * * * *